(12) United States Patent
Hum et al.

(10) Patent No.: US 8,753,708 B2
(45) Date of Patent: Jun. 17, 2014

(54) SOLVENTLESS METHOD FOR FORMING A COATING ON A MEDICAL ELECTRICAL LEAD BODY

(75) Inventors: Larry L. Hum, Cottage Grove, MN (US); James Q. Feng, Maple Grove, MN (US); Arienne P. Simon, Harrison City, PA (US); Tolga Tas, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 840 days.

(21) Appl. No.: 12/832,635

(22) Filed: Jul. 8, 2010

(65) Prior Publication Data

US 2011/0052787 A1 Mar. 3, 2011

Related U.S. Application Data

(60) Provisional application No. 61/239,117, filed on Sep. 2, 2009, provisional application No. 61/335,039, filed on Dec. 30, 2009.

(51) Int. Cl.
*A61L 33/00* (2006.01)

(52) U.S. Cl.
USPC ........ 427/2.1; 264/250; 174/126.1; 623/1.34; 623/1.53; 607/120; 427/2.11; 427/2.12; 427/2.14; 427/2.21; 427/2.22; 427/2.24; 427/58; 427/430.1

(58) Field of Classification Search
USPC ........ 607/120; 623/1.34; 174/126.1; 264/250
See application file for complete search history.

(56) References Cited

U.S. PATENT DOCUMENTS

| | | | |
|---|---|---|---|
| 4,928,689 | A | 5/1990 | Hauser |
| 5,103,837 | A | 4/1992 | Weidlich et al. |
| 5,282,844 | A | 2/1994 | Stokes et al. |
| 5,324,324 | A | 6/1994 | Vachon et al. |
| 5,385,579 | A | 1/1995 | Helland |
| 5,766,527 | A | 6/1998 | Schildgen et al. |

(Continued)

FOREIGN PATENT DOCUMENTS

| | | |
|---|---|---|
| EP | 1554990 | 7/2005 |
| JP | 8-10338 | 1/1996 |

(Continued)

OTHER PUBLICATIONS

NuSil Med-6210 Product Profile, 2013, http://www.nusil.com/library/products/MED-6210P.pdf.*

(Continued)

*Primary Examiner* — Dah-Wei D Yuan
*Assistant Examiner* — Andrew Bowman
(74) *Attorney, Agent, or Firm* — Faegre Baker Daniels LLP

(57) ABSTRACT

A solventless method for forming a coating on a medical electrical lead is described. The method includes combining particles of a therapeutic agent with a polymeric material in a flowable form in the absence of a solvent to form a uniform suspension. A predetermined amount of the suspension is dispensed onto a portion of the lead and is then cured to form the therapeutic agent eluting layer. Additional layers such as a primer layer, fluoro-opaque layer and/or a topcoat layer can be formed using the solventless method. Employing a solventless method may avoid contraction of the layer being formed due to solvent evaporation during the curing process, and may facilitate greater control over the thickness of the therapeutic agent eluting coating.

24 Claims, 9 Drawing Sheets

(56) References Cited

U.S. PATENT DOCUMENTS

| | | | |
|---|---|---|---|
| 5,837,313 | A | 11/1998 | Ding et al. |
| 5,853,652 | A | 12/1998 | Schildgen et al. |
| 5,987,746 | A | 11/1999 | Williams et al. |
| 5,991,667 | A | 11/1999 | Feith |
| 6,253,110 | B1 | 6/2001 | Brabec et al. |
| 6,284,682 | B1 | 9/2001 | Troczynski et al. |
| 6,361,780 | B1 | 3/2002 | Ley et al. |
| 6,363,286 | B1 | 3/2002 | Zhu et al. |
| 6,426,114 | B1 | 7/2002 | Troczynski et al. |
| 6,635,214 | B2 * | 10/2003 | Rapacki et al. ............... 264/250 |
| 6,709,514 | B1 | 3/2004 | Hossainy |
| 6,730,324 | B2 | 5/2004 | Troczynski et al. |
| 6,770,325 | B2 | 8/2004 | Troczynski et al. |
| 6,889,092 | B2 | 5/2005 | Zhu et al. |
| 6,896,965 | B1 | 5/2005 | Hossainy |
| 7,115,300 | B1 | 10/2006 | Hossainy |
| 7,174,221 | B1 | 2/2007 | Chen et al. |
| 7,247,364 | B2 | 7/2007 | Hossainy et al. |
| 7,279,175 | B2 | 10/2007 | Chen et al. |
| 7,881,808 | B2 | 2/2011 | Borgaonkar et al. |
| 2001/0021873 | A1* | 9/2001 | Stinson ........................ 623/1.34 |
| 2002/0022826 | A1 | 2/2002 | Reynolds et al. |
| 2002/0138123 | A1 | 9/2002 | Casas-Bejar et al. |
| 2003/0028231 | A1* | 2/2003 | Partridge et al. ............. 607/120 |
| 2003/0031699 | A1 | 2/2003 | Van Antwerp |
| 2003/0073961 | A1 | 4/2003 | Happ |
| 2003/0093136 | A1 | 5/2003 | Osypka et al. |
| 2003/0198821 | A1 | 10/2003 | Terry et al. |
| 2004/0037886 | A1 | 2/2004 | Hsu |
| 2004/0063805 | A1 | 4/2004 | Pacetti et al. |
| 2005/0070985 | A1 | 3/2005 | Knapp et al. |
| 2005/0080470 | A1 | 4/2005 | Westlund et al. |
| 2005/0180919 | A1 | 8/2005 | Tedeschi |
| 2006/0235499 | A1 | 10/2006 | Heil, Jr. et al. |
| 2007/0051531 | A1* | 3/2007 | Borgaonkar et al. ...... 174/126.1 |
| 2007/0128246 | A1 | 6/2007 | Hossainy et al. |
| 2007/0190104 | A1 | 8/2007 | Kamath et al. |
| 2007/0239245 | A1 | 10/2007 | Borgaonkar et al. |
| 2008/0009939 | A1 | 1/2008 | Gueriguian et al. |
| 2008/0051866 | A1 | 2/2008 | Chen et al. |
| 2008/0167710 | A1 | 7/2008 | Dave et al. |
| 2009/0054961 | A1 | 2/2009 | Borgaonkar et al. |

FOREIGN PATENT DOCUMENTS

| | | |
|---|---|---|
| JP | 10-140078 | 5/1998 |
| JP | 2007-186804 | 7/2007 |
| JP | 2008-515611 | 5/2008 |
| WO | WO 02/13785 | 2/2002 |
| WO | WO 2005/035655 | 4/2005 |
| WO | WO 2006-070947 | 7/2006 |
| WO | WO 2007/030722 | 3/2007 |
| WO | WO 2007/126806 | 11/2007 |
| WO | WO 2009/051945 | 4/2008 |
| WO | WO 2008-091886 | 7/2008 |

OTHER PUBLICATIONS

International Search Report and Written Opinion issued in PCT/US2007/007558 mailed Sep. 20, 2007.

Office Action issued in EP App 07754128.2, Mailed Feb. 19, 2009, 3 pages.

Response filed Aug. 31, 2009 to Office Action dated Feb. 19, 2009, EP App 07754128.

Office Action issued in EP 07754128 mailed Mar. 31, 2010.

International Preliminary Report on Patentability, Chapter II, issued in PCT/US2006/035064, dated Sep. 12, 2007, 12 pages.

International Search Report and Written Opinion issued in PCT/US2006/035064, filed Jan. 23, 2007.

Kirby, Darren, "Use of a Bioactive Material on a Pacemaker Electrode for the Purpose of Enhancing Heart Pace/Sense Efficiency", MSC Biomedical Engineering, Thesis, Thrinty College Dublin (2003).

York, P., "New Materials and Systems for Drug Delivery and Targeting", Chemical Aspects of Drug Delivery Systems, Copyright 1996, pp. 1-10, proceedings from a symposium held Apr. 17-18, 1996 at Salford University.

International Search Report and Written Opinion issued in PCT/US2010/041694, mailed Feb. 4, 2011, 11 pages.

* cited by examiner

Fig. 2B  Fig. 2C

50 wt. % Tungsten

SOLVENTLESS METHOD FOR FORMING A COATING ON A MEDICAL ELECTRICAL LEAD BODY

CROSS REFERENCE TO RELATED APPLICATION

This application claims the benefit under 35 U.S.C. §119 of U.S. Provisional Application No. 61/239,117, filed on Sep. 2, 2009, entitled "Solventless Method for Forming a Therapeutic Agent Eluting Coating on a Medical Electrical Lead," which is incorporated herein by reference in its entirety for all purposes. This application also claims the benefit under 35 U.S.C. §119 of U.S. Provisional Application No. 61/335,039, filed on Dec. 30, 2009, entitled "Solventless Method for Forming a Fluoro-opaque Coating on a Medical Electrical Lead," which is also incorporated herein by reference in its entirety for all purposes.

TECHNICAL FIELD

This invention relates to medical electrical leads including a coating. More particularly, the present invention is directed to a solventless method for forming a coating on a medical electrical lead.

BACKGROUND

Leads having electrodes implanted in or about the heart have been used to reverse life-threatening arrhythmia or to stimulate contraction of the heart. Electrical energy is applied to the heart via an electrode to return the heart to normal rhythm. Leads are usually positioned on or in the ventricle or the atrium and the lead terminals are attached to a pacemaker or defibrillator which is implanted subcutaneously.

One issue concerning, for example, pacemaker leads is the increase in stimulation threshold, both acute and chronic, caused by the interaction between the electrode and body tissue at the point of implant. Approaches to reducing the threshold include the incorporation of drug collars or plugs containing a therapeutic agent such as, for example, dexamethasone or beclomethasone into the lead body. However, the size of the plug or collar required to deliver a therapeutically effective amount of the therapeutic agent prevents a substantial reduction in the overall lead body diameter. Moreover, these devices many not adequately address many of the physiological processes involved in the healing response upon lead implantation.

Another issue concerning pacemaker leads is the difficulty in designing a lead body with fluoropacity for visualization during and after implantation of the lead in a patient's body. Current technology places a radiopaque ring on the lead body for visualization of the lead in viva Radiopaque rings are not amenable to irregular lead body shapes and, again, the size of the radiopaque ring may prevent a substantial reduction in the overall lead body diameter.

SUMMARY

Example 1 is a solventless method for forming a therapeutic agent eluting coating on a medical electrical lead including a lead body comprising: 1) dispensing a predetermined amount of a solventless suspension onto an outer surface of the lead body in close proximity to at least one electrode located on the lead body using an automated syringe while rotating the lead body around its longitudinal axis, the suspension comprising up to about 20 wt % particles of at least one therapeutic agent dispersed within an uncured silicone medical adhesive having a viscosity ranging from about 0.001 Pas to about 20 Pas; and 2) curing the suspension to form a polymer matrix layer that is free of residual solvent.

In Example 2, the method according to Example 1, wherein the therapeutic agent comprises an anti-inflammatory agent.

In Example 3, the method according to any one of Examples 1 and 2, wherein the therapeutic agent comprises an anti-proliferative agent.

In Example 4, the method according to any one of Examples 1-3, wherein the therapeutic agent comprises a combination of an anti-inflammatory agent and an anti-proliferative agent.

In Example 5, the method according to any one of Examples 1-4, wherein the therapeutic agent comprises dexamethasone or a derivative or salt thereof.

In Example 6, the method according to any one of Examples 1-5, wherein the uncured silicone medical adhesive comprises NuSil MED-6210.

In Example 7, the method according to any one of Examples 1-6, wherein the uncured silicone medical adhesive comprises NuSil MED-6215.

In Example 8, the method according to any one of Examples 1-7, wherein the step of combining an uncured medical adhesive and at least one therapeutic agent further comprises admixing particles of a fluoro-opaque material into the suspension.

In Example 9, the method according to Example 8, wherein the fluoro-opaque material comprises tungsten particles.

In Example 10, the method according to Example 8, wherein the fluoro-opaque material comprises platinum particles.

In Example 11, the method according to any one of Examples 1-10, further comprising the steps of: dispensing a predetermined amount of an uncured admixture substantially free of solvent comprising an uncured silicone adhesive having a viscosity ranging from about 0.001 Pas to about 20 Pas and particles of a fluoro-opaque material onto the outer surface of the lead body at a location in close proximity to the at least one electrode using a motorized syringe while rotating the lead body around its longitudinal axis; and curing the admixture to form a fluoro-opaque layer.

In Example 12, the method according to any one of Examples 1-11, wherein the fluoro-opaque material comprises tungsten or platinum particles.

In Example 13, the method according to any one of Examples 1-12, wherein the fluoro-opaque particles comprise tungsten particles.

In Example 14, the method according to any one of Examples 1-13, wherein the fluoro-opaque particles comprise platinum particles.

In Example 15, the method according to any one of Examples 1-14, wherein an amount of fluoro-opaque particles in the admixture ranges from about 10 wt % to about 80%.

In Example 16, the method according to any one of Examples 1-15, wherein an amount of fluoro-opaque particles in the admixture is at least 50 wt %.

In Example 17, the method according to any one of Examples 1-16, wherein an amount of fluoro-opaque particles in the admixture ranges from about 50 wt % to about 75 wt %.

In Example 18, the method according to any one of Examples 1-17, wherein the fluoro-opaque layer is formed over the polymer matrix layer.

In Example 19, the method according to any one of Examples 1-18, wherein the polymer matrix layer is formed over the fluoro-opaque layer.

In Example 20, the method according to any one of claims 1-19, wherein the fluoro-opaque layer is formed over and in contact with the outer surface of the lead body.

In Example 21, the method according to any one of claims 1-20, further comprising the steps of: dispensing a predetermined amount of an uncured topcoat material in the absence of solvent onto the fluoro-opaque layer using a motorized syringe while simultaneously rotating the lead body; and curing the topcoat material to form a topcoat layer disposed over and in contact with the fluoro-opaque layer.

In Example 22, the method according to any one of claims 1-21, further comprising the steps of: dispensing a predetermined amount of a primer material substantially free of solvent onto the outer surface of the lead body at a location in close proximity to the at least one electrode using a motorized syringe while rotating the lead body around its longitudinal axis; curing the primer material to form a primer layer; and thereafter, forming the polymer matrix layer over the primer layer.

In Example 23, the method according to any one of claims 1-22, further comprising dispensing a predetermined amount of a primer material substantially free of solvent onto the outer surface of the lead body at a location in close proximity to the at least one electrode using a motorized syringe while rotating the lead body around its longitudinal axis, curing the primer material to form a primer layer, and thereafter forming a fluoro-opaque layer over and in contact with the primer layer.

In Example 24, the method according to any one of claims 1-23, further comprising dispensing a predetermined amount of an uncured topcoat material in the absence of solvent onto the polymer matrix layer using a motorized syringe while simultaneously rotating the lead body.

In Example 25, the method according to any one of claims 1-24, wherein the uncured topcoat material comprises a therapeutic agent admixed therein.

In Example 26, the method according to any one of claims 1-25, wherein the topcoat material comprises the same silicone medical adhesive as the polymer matrix layer material.

In Example 27, the method according to any one of claims 1-26, wherein the uncured topcoat material comprises phosphorylcholine.

In Example 28, the method according to any one of claims 1-27, wherein the uncured topcoat material comprises hyaluronic acid.

In Example 29, the method according to any one of claims 1-28, wherein a percentage of therapeutic agent in the suspension ranges from about 2 to about 20% (wt/wt).

In Example 30, the method according to any one of claims 1-29, wherein a percentage of therapeutic agent in the suspension ranges from about 5 to about 20% (wt/wt).

In Example 31, A solventless method of forming a multilayered coating on a medical electrical lead including a lead body comprising: 1) dispensing a predetermined amount of a solventless admixture comprising an uncured silicone adhesive having a viscosity ranging from about 0.001 Pas to about 20 Pas and particles of a fluoro-opaque material onto the outer surface of the lead body at a location in close proximity to the at least one electrode while rotating the lead body around its longitudinal axis; 2) curing the admixture to form a fluoro-opaque layer, wherein the fluoro-opaque layer comprises about 10 wt % to about 80 wt % of the fluoro-opaque material; 3) dispensing a predetermined amount of a solventless suspension comprising up to about 20% (wt/wt) of therapeutic agent particles distributed within the uncured silicone medical adhesive having a viscosity ranging from about 0.001 Pas to about 20 Pas over the fluoro-opaque layer using an automated syringe while rotating the lead body around its longitudinal axis; and 4) curing the suspension to form a polymer matrix layer that is free of residual solvent.

In Example 32, the method according to Example 31, further comprising dispensing a predetermined amount of an uncured topcoat material in the absence of solvent onto the fluoro-opaque layer using a motorized syringe while simultaneously rotating the lead body; and curing the topcoat material to form a topcoat layer disposed over and in contact with the fluoro-opaque layer.

In Example 33, the method according to any one of Examples 31-32, further comprising dispensing a predetermined amount of a primer material substantially free of solvent onto the outer surface of the lead body at a location in close proximity to the at least one electrode using a motorized syringe while rotating the lead body around its longitudinal axis, curing the primer material to form a primer layer, and thereafter forming the fluoro-opaque layer over and in contact with the primer layer.

In Example 34, the method according to any one of Examples 31-33, wherein the therapeutic agent comprises dexamethasone or a derivative or salt thereof.

In Example 35, the method according to any one of Examples 31-34, wherein the uncured silicone medical adhesive comprises NuSil MED-6210 or NuSil MED-6215.

In Example 36, the method according to any one of Examples 31-35, wherein the fluoro-opaque material comprises tungsten particles.

In Example 37, the method according to any one of Examples 31-36, wherein the fluoro-opaque material comprises platinum particles.

In Example 38, the method according to any one of Examples 31-37, wherein an amount of fluoro-opaque particles in the admixture is at least 50 wt %.

In Example 39, the method according to any one of Examples 31-38, wherein an amount of fluoro-opaque particles in the admixture ranges from about 50 wt % to about 75 wt %.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 2A-2D are schematic views of a portion of a lead including a coating according to various embodiments of the present invention.

Figure 1:
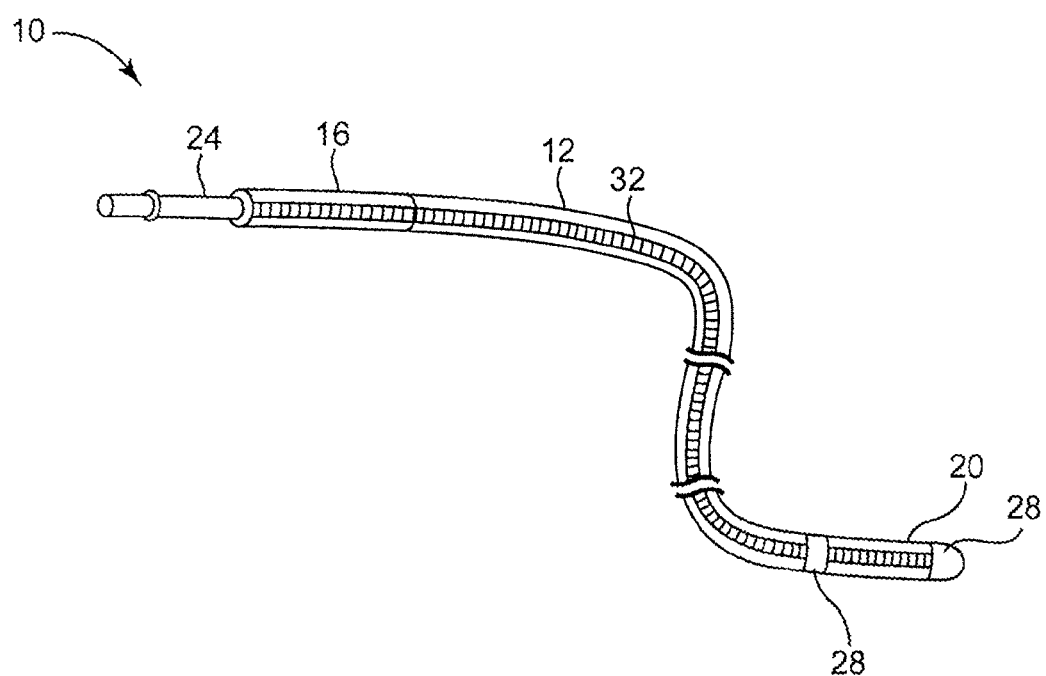
FIG. 1 is a schematic view of a medical electrical lead according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended embodiments.

DETAILED DESCRIPTION

FIG. 1 is a partial cross-sectional view of a medical electrical lead 10, according to various embodiments of the present invention. According to some embodiments, the medical electrical lead 10 can be configured for implantation within a patient's heart. According to other embodiments, the medical electrical lead 10 is configured for implantation within a patient's neurovascular regions. In yet another embodiment, the lead 10 can be a lead for a cochlear implant. The medical electrical lead 10 includes an elongated, insulative lead body 12 extending from a proximal end 16 to a distal end 20. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors are employed, the lead can include a combination of coiled and cable conductors. When a coiled conductor is employed, according to some embodiments, the conductor can have either a co-radial or a co-axial configuration.

The lead body 12 is flexible, but substantially non-compressible along its length, and has a circular cross-section. According to one embodiment of the present invention, an outer diameter of the lead body 12 ranges from about 2 to about 15 French. In many embodiments, the lead body 12 does not include a drug collar or plug.

The medical electrical lead 10 can be unipolar, bipolar, or multi-polar depending upon the type of therapy to be delivered. In embodiments of the present invention employing multiple electrodes 28 and multiple conductors 32, each conductor 32 is adapted to be connected to an individual electrode 28 in a one-to-one manner allowing each electrode 28 to be individually addressable. Additionally, the lead body 12 can include one or more lumens adapted to receive a guiding element such as a guidewire or a stylet for delivery of the lead 10 to a target location within a patient's heart.

The electrodes 28 can have any electrode configuration as is known in the art. According to one embodiment of the present invention, at least one electrode can be a ring or partial ring electrode. According to another embodiment, at least one electrode 28 is a shocking coil. According to yet another embodiment of the present invention, at least one electrode 28 includes an exposed electrode portion and an insulated electrode portion. In some embodiments, a combination of electrode configurations can be used. The electrodes 28 can be coated with or formed from platinum, stainless steel, MP35N, a platinum-iridium alloy, or another similar conductive material.

According to various embodiments, the lead body 12 can include one or more fixation members for securing and stabilizing the lead body 12 including the one or more electrodes 28 at a target site within a patient's body. The fixation member(s) can be active or passive. An exemplary active fixation member includes a screw-in fixation member. Examples of passive fixation include pre-formed distal portions of the lead body 12 adapted to bear against the vessel walls and/or expandable tines provided at the distal end of the lead body 12.

FIGS. 2A-2D depict a therapeutic agent eluting coating 30 provided on at least a portion of the lead body 12 according to various embodiments of the present invention. According to one embodiment, the coating 30 is provided over one or more discrete sections located along an outer surface 34 of the lead body 12. According to another embodiment, the coating 30 is provided over a majority (e.g. 60-95%) of the outer surface of the lead body 12 extending from the proximal end 16 to the distal end 20 of the lead body 12. According to yet another embodiment, the coating 30 is provided on the outer surface 34 of the lead body 12 in close proximity to at least one electrode 28. According to still another embodiment, the coating 30 is provided over a distal portion of the lead body 12 such that it is adjacent to at least one electrode 28. Although the coating 30 can be provided over at least a portion of the electrode 28, in certain applications it may be beneficial to allow the electrode to remain free of coating so that the pacing function of the electrode is not impacted.

According to various embodiments, a shown in FIG. 2B, the coating 30 includes at least one polymer matrix layer 44. In one embodiment, the polymer matrix layer 44 includes one or more therapeutic agents admixed therein. In another embodiment, the polymer matrix layer 44 can include particles of a fluoro-opaque material in addition to the one or more therapeutic agents admixed therein. Upon implantation of the lead 10 at a desired location in a patient's body, the therapeutic agent or agents are released from the polymer matrix layer 44.

In other embodiments, as shown in FIG. 2C, the coating 30 also includes a primer layer 46. The primer layer 46 is deposited onto the outer surface 34 of the lead body 12 such that it is disposed between the outer surface of the lead body 12 and the polymer matrix layer 44. The primer layer 46 facilitates adhesion of the polymer matrix layer 44 and other layers to the outer surface 34 of the lead body 12.

Figure 2A:
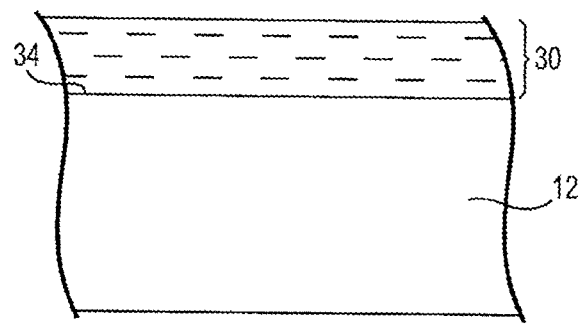
Figure 2D:
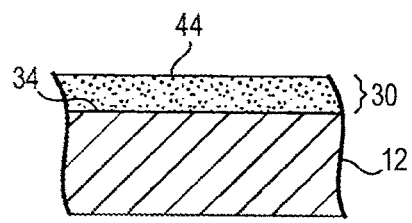
Figure 2D:
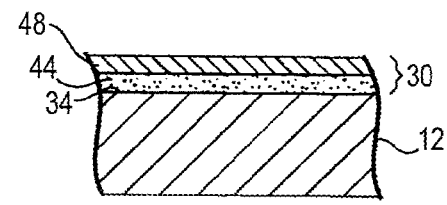
Figure 2D:
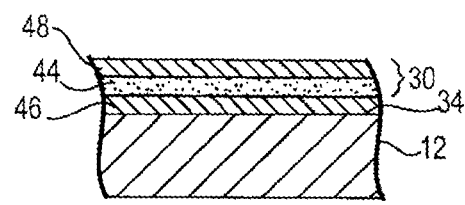

In some embodiments, as shown in FIG. 2D, the coating 30 also includes at least one topcoat layer 48. The topcoat layer 48 can be used to control the rate of release of the therapeutic agent from the polymer matrix layer 44. In one embodiment, one or more topcoat layers 48 are disposed over and in contact with the polymer matrix layer 44. In some embodiments, the topcoat layer 48 also can include a therapeutic agent. The therapeutic agent included in the topcoat layer 48 can be the same as or different from the therapeutic agent included in the polymer matrix layer 44. For example, the topcoat layer 48 can be configured to provide an initial burst of therapeutic agent into the surrounding environment. Additional top or intermediate layers may also be utilized.

Figure 3A:
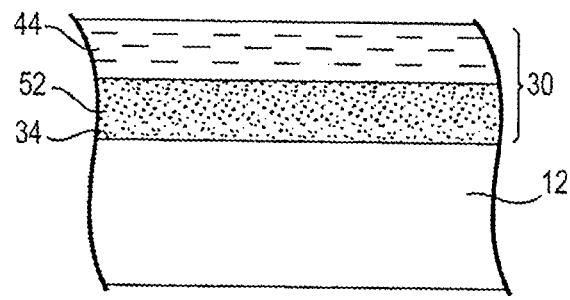
FIGS. 3A-3C are schematic views of a portion of a lead including a coating according to other various embodiments of the present invention.
Figure 3B:
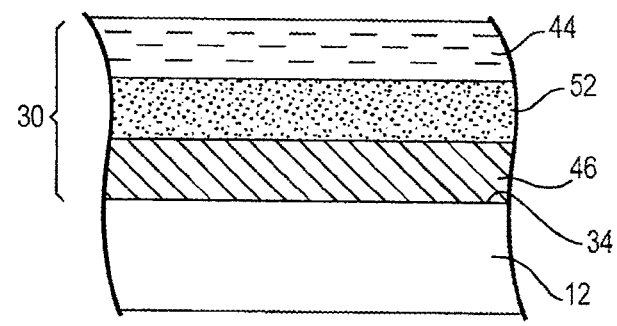
Figure 3C:
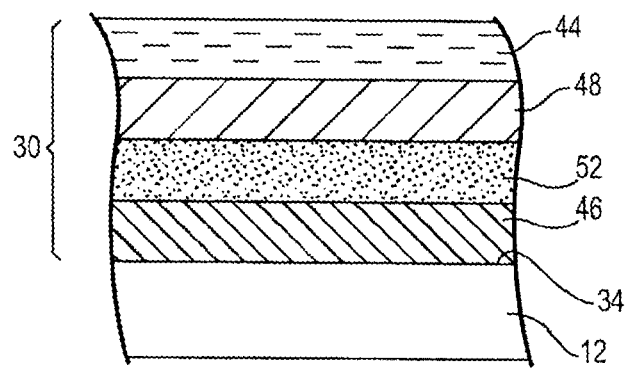

According to other embodiment of the present invention as shown in FIGS. 3A-3C, the therapeutic agent eluting coating 30 includes at least one polymer matrix layer 44 that contains a therapeutic agent and at least one fluoro-opaque layer 52. In certain embodiments, multiple fluoro-opaque layers 52 can be used. The fluoro-opaque layer(s) 52 is provided to assist delivery of the lead by the clinician implanting the lead using standard visualization techniques and may also be used in follow-up visits with the patient to identify any potential complications such as dislodgment of the lead from the implant site. In one embodiment, as shown in FIG. 3A, the fluoro-opaque layer 52 is deposited onto the outer surface 34 of the lead body 12 such that it is disposed between the outer surface of the lead body 12 and the polymer matrix layer 44 including a therapeutic agent. As shown in FIG. 3B, a primer layer 46 may be used to promote adhesion between the fluoro-opaque layer 52 and the outer surface 34 of the lead body 12. In some embodiments, a topcoat layer 48 can be provided over the fluoro-opaque layer as shown in FIG. 3C. The topcoat layer 48 is provided over the fluoro-opaque layer 52 to prevent degradation of the fluoro-opaque layer and release of the fluoro-opaque agent contained within the fluoro-opaque layer into the body environment.

Each of the individual layers (polymer matrix 44, primer 46, topcoat 48 and fluoro-opaque 52) can be formed using a solventless suspension. In one embodiment, a solventless suspension is a suspension having less than about 5% by volume solvent and more particularly less than about 1% by volume solvent. In still another embodiment, a solventless suspension is completely free from any solvents. Additionally, a solventless coating composition can be described as a coating composition having no residual solvents in its cured or solid state. In one embodiment, for example, when the solventless suspension is in its cured or solid state it has less than about 1% residual solvents and more particularly less than about 0.5% residual solvents. In still another embodiment, the solventless suspension is completely free of residual solvents in its cured or solid state.

Using a solventless method to form the individual layers (polymer matrix 44, primer 46, topcoat 48 and fluoro-opaque 52) of the coating 30 has certain advantages. These advantages may include minimizing contraction of the coating 30 during curing and preventing or minimizing solvent extraction of the therapeutic agent from the polymer matrix layer 44. Additionally, using a solvent-free suspension to form the individual coating layers may also prevent degradation of the therapeutic agent by the solvent which may result in a more predictable drug release profile. Finally, employing a solventless coating composition for forming the individual coating layers may be easier to apply to the lead body and may result in a more uniform dispersion of the therapeutic agent coating. For example, using a solventless coating composition may limit slumping of the coating composition prior to curing of the coating on the lead body.

The polymer matrix layer 44 can include a single polymer or a combination of polymers provided in a liquid or flowable form. In one embodiment the polymeric material used to form the polymer matrix layer 44 is in an uncured state when the therapeutic agent is added. In another embodiment, the polymeric material can be provided in a melt form. A polymer melt is a polymer or combination of polymers in a non-solid state or is modified by exposure to a temperature equal to or greater than the melting temperature of the polymer. If a combination of polymers is used, the melting temperature of the polymeric material having the highest melting temperature is reached or surpassed.

Several factors can be taken into account when selecting a suitable polymeric material for the solventless method of forming the individual layers of the coating 30. Such factors include the viscosity of the polymeric material, the workable pot life of the polymeric material, and its shear rate, among others. In one embodiment, the polymeric material can be selected such that it has a viscosity range that allows particles of the therapeutic agent to remain uniformly suspended until cured while still allowing for automated dispensing through, for example, a syringe.

Selecting a polymeric material having a suitable viscosity may improve the suspension and may reduce the number of combination steps and may reduce the processing time for forming the each of the individual layers on the outer surface 34 of the lead body 12. However, the viscosity cannot be so high as to prevent automated dispensing. In one embodiment, the polymeric material has a viscosity ranging from about 100 mPas to about 100 Pas. In another embodiment, the polymeric material has a viscosity ranging from about 0.001 Pas to about 20 Pas. In still other embodiments, the polymeric material has a viscosity ranging from about 1 Pas to about 20 Pas.

Suitable polymeric materials for the polymer matrix layer 44 include medical adhesives, and more particularly, silicone-based medical adhesives having a viscosity within the range discussed above. Exemplary silicone-based medical adhesives include NuSil MED-6210 or MED-6215 polymer available from NuSil Technology LLC, Carpenteria, Calif. Other suitable medical adhesives include moisture curable medical adhesives, UV curable medical adhesives, and platinum cure silicones. The moisture curable and UV curable medical adhesives may or may not be silicone based. Exemplary moisture curable adhesives include oxime and ethoxy cure silicones. An exemplary UV curable medical adhesive includes UV cure silicone.

Any drug or bioactive agent which can serve as a useful therapeutic agent when released into a patient can be combined with the polymeric material to provide a solventless suspension for forming the polymer matrix layer 44. In one embodiment, particles of the therapeutic agent are admixed with the polymeric material such that the particles are uniformly dispersed throughout the polymeric material.

The therapeutic agent can include a single therapeutic agent or a combination of different therapeutic agents. Exemplary therapeutic agents include anti-inflammatory and anti-proliferative agents. More specifically, exemplary therapeutic agents can include, but are not limited to: paclitaxel; clobetasol; rapamycin; sirolimus; everolimus; tacrolimus; actinomycin-D; dexamethasone (e.g., dexamethasone, dexamethasone sodium phosphate or dexamethasone acetate); betamethasone; mometasone furoate; vitamin E; mycophenolic acid; cyclosporins; beclomethasone (e.g., beclomethasone dipropionate anhydrous); and derivatives, analogs, salts; and combinations thereof.

The polymer material and therapeutic agent can be combined in suspension in amounts that result in a polymer matrix layer 44 having an effective percentage (wt of agent/total weight of matrix X 100%) of therapeutic agent in the polymer matrix layer 44. Because a solventless composition is used to form the suspension the percentage (wt/wt %) of therapeutic agent in the suspension is substantially equal to the percentage (wt/wt %) of the therapeutic agent of the cured polymer matrix layer 44. In one embodiment, the polymer matrix layer 44 achieves a drug release profile substantially equal to the drug release profile obtained from a traditional monolithic controlled release device such as, for example, a drug collar employing the same or similar materials.

Additionally, the percentage of therapeutic agent in the polymer matrix layer 44 can be adjusted such that the drug release profile is immediate, short term, or sustained release. A polymer matrix layer having an immediate release profile releases the therapeutic agent content within minutes to about an hour after implantation. A polymer matrix layer having a short term release profile more slowly liberates the content within days to weeks following implantation. Finally, a polymer matrix layer having a sustained release profile releases the content very slowly, with full release requiring months to years.

According to one embodiment, the percentage of therapeutic agent in the polymer matrix layer 44 ranges from about 2 to about 35% (wt/wt). According to another embodiment, the percentage of therapeutic agent in the polymer matrix layer 44 ranges from about 5 to about 20% (wt/wt). Typically, a polymer matrix layer 44 including a higher percentage of therapeutic agent in the matrix will have a faster drug release profile. Additionally, the selection of the polymer included in the polymer matrix layer 44 can also affect the release rate of the therapeutic agent.

In one embodiment, the polymer matrix layer 44 can also include particles of fluoro-opaque material in addition to the one or more therapeutic agents. Particles, including fibers or crystals, of any fluoro-opaque or radiopaque materials which can provide sufficient fluoro-opacity or radiopacity can be combined with the various polymeric materials, described above. Typically, the fluoro-opaque material is a non-biodegradable fluoro-opaque material and is suitable for long term implantation within a patient's body. In one embodiment, particles of the fluoro-opaque material are admixed with the polymeric material such that the particles are dispersed throughout the polymeric material. In another embodiment, particles of the fluoro-opaque material are admixed with the polymeric material such that the particles are substantially uniformly dispersed throughout the polymeric material. In some embodiments, the particles can have an average particle size ranging from about 1 nm to about 100 nm. In yet another embodiment, the particles can have an average particle size ranging from about 6 nm to about 12 nm.

Exemplary fluoro-opaque materials include, but are not limited to iodine and its salts or compounds, barium and its salts or compounds, tungsten, rhenium, osmium, noble metals, palladium, gold, colloidal gold, silver, platinum, tantalum, iridium or their alloys. Such materials are highly visible by fluoroscopy and are therefore visible even when the layer 44 is provided at a minimal thickness. In one embodiment, the fluoro-opaque material is tungsten. In another embodiment, the fluoro-opaque material is platinum.

According to some embodiments, the primer layer 46 is also formed by dispensing a solventless polymer material onto the outer surface 34 of the lead body 12 prior to the application of the suspension that forms the polymer matrix layer 44. The polymeric material used to form the primer layer 46 is also selected based on its viscosity. In one embodiment, the viscosity of the polymeric material used to form the primer layer ranges from about 100 mPas to about 100 Pas and, more particularly, from about 0.001 Pas to about 20 Pas. Suitable materials for forming the primer layer 46 include silicone based medical adhesives (such as those also used to form the polymer matrix layer), epoxy resins, and acrylics including polyacrylates and polymethacrylates. In one embodiment, the primer layer 46 is formed from polybutylmethacrylate (PBMA).

In another embodiment, the outer surface 34 of the lead body 12 is treated using various surface treatment techniques to provide the primer layer 46. For example, the outer surface 34 can be modified using plasma surface treatment techniques such that the primer layer 46 and any additional layers can better adhere to the outer surface 34.

Like the polymer matrix layer 44, the topcoat layer 48 is generally formed by dispensing a solventless silicone-based medical adhesive onto the polymer matrix layer 44. The topcoat layer 48 may control the rate of release of the therapeutic agent from the polymer matrix layer 44. In some cases, the topcoat layer 48 includes a therapeutic agent to affect the drug release profile of the coating 30. In other embodiments, the topcoat layer 48 includes no therapeutic agent such that it slows the release of the therapeutic agent from the matrix layer 44 into the tissue. The effect that the topcoat layer 48 provides over the rate of release of the therapeutic agent from the polymer matrix layer 44 depends on a variety of factors including: the material selected for the topcoat layer 48, the number of topcoat layers 48 applied over the polymer matrix layer 44, and the thickness and/or porosity of each topcoat layer 48.

The topcoat layer 48 can be formed from the same or different polymeric material used to form the polymer matrix layer 44. For example, in one embodiment, the same silicone based medical adhesive used to form the polymer matrix layer 44 is used to form the topcoat layer 48. Additional exemplary polymeric materials suitable for forming the topcoat layer 48 include, but are not limited to: polyurethanes, silicones, silicone elastomers, and polyvinylidene halides or their copolymers such as polyvinylidene fluoride (PVDF) and poly(vinylidene fluoride-co-hexafluoropropylene).

In other embodiments the topcoat layer 48 can be formed from a bio-beneficial material. Exemplary bio-beneficial materials for the topcoat layer 48 include but are not limited to phosphorylcholine (PC) and hyaluronic acid (HA). In still other embodiments, the topcoat layer 48 includes one or more therapeutic agents admixed with one or more polymeric materials, described above.

Like the other layers (polymer matrix layer 44, primer layer 46 and topcoat layer 48), the fluoro-opaque layer 52 can also be formed using a solventless method. The particles, including fibers, of any fluoro-opaque or radiopaque materials which can provide sufficient fluoro-opacity or radiopacity can be combined with the various polymeric materials, described above used to form the other layers (polymer matrix 44, primer layer 46 and topcoat layer 48), to provide a solventless suspension for forming the fluoro-opaque layer 52. Typically, the fluoro-opaque material is a non-biodegradable fluoro-opaque material and is suitable for long term implantation within a patient's body. In one embodiment, particles of the fluoro-opaque material are admixed with the polymeric material such that the particles are uniformly dispersed throughout the polymeric material. In some embodiments, the particles can have an average particle size ranging from about 1 nm to about 100 nm. In yet another embodiment, the particles can have an average particle size ranging from about 6 nm to about 12 nm. Exemplary fluoro-opaque materials include, but are not limited to iodine and its salts or compounds, barium and its salts or compounds, tungsten, rhenium, osmium, noble metals, palladium, gold, colloidal gold, silver, platinum, tantalum, iridium or their alloys. Such materials are highly visible by fluoroscopy and are therefore visible even when the layer 52 is provided at a minimal thickness. In one embodiment, the fluoro-opaque material is tungsten. In another embodiment, the fluoro-opaque material is platinum.

The polymer material and fluoro-opaque material can be combined to form a suspension in amounts that result in a fluoro-opaque layer 52 having a sufficient amount of fluoro-opaque material to be detected using standard visualization techniques (e.g., fluoroscopy). Multiple fluoro-opaque layers 52 can also be used to achieve the desired level of fluoro-opacity. Because a solventless composition is used to form the suspension the percentage (wt/wt %) of fluoro-opaque material in the suspension is substantially equal to the percentage (wt/wt %) of the fluoro-opaque material of the cured fluoro-opaque layer 52. In one embodiment, the amount of fluoro-opaque material included in the suspension used to form an individual fluoro-opaque coating layer 52 ranges from about 10 wt. % to about 80 wt. % of the total weight of the suspension. In another embodiment, the amount of fluoro-opaque material included in the suspension ranges from about 20 wt. % to about 50 wt. % of the total weight of the suspension. In yet another embodiment, the amount of fluoro-opaque material included in the suspension ranges from about 50 wt. % to about 80 wt. % of the total weight of the suspension. In still another embodiment, the amount of fluoro-opaque material included in the suspension used to form an individual fluoro-opaque layer 52 ranges from about 10 wt. % to about 20 wt. % of the total weight of the suspension. In yet still another embodiment, the amount of fluoro-opaque material included in the suspension used to form an individual fluoro-opaque layer 52 is approximately 75 wt. %.

Figure 4:
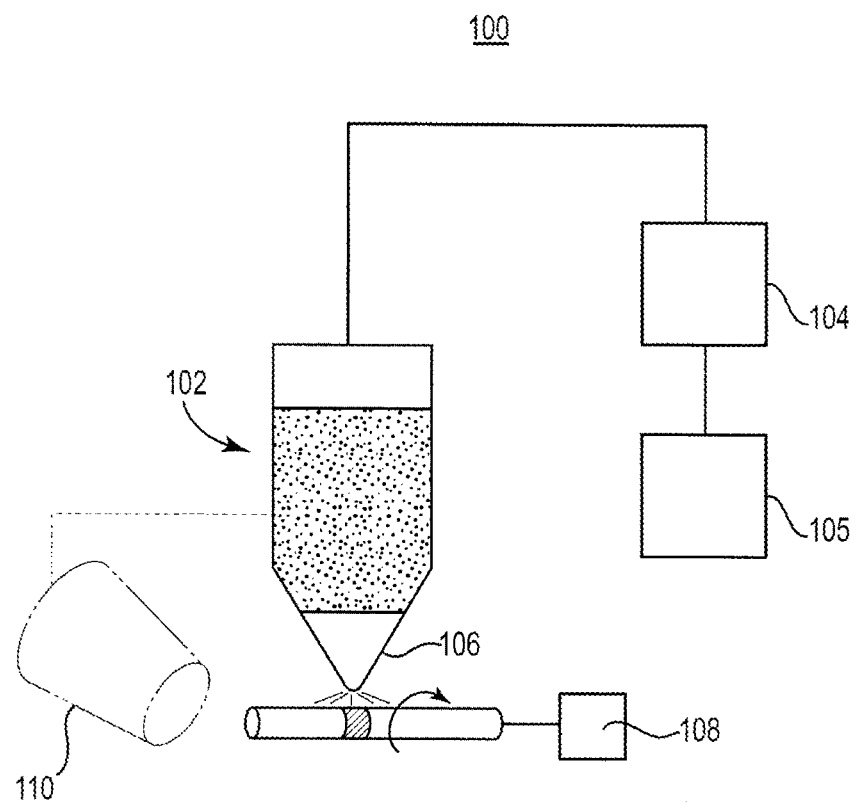
FIG. 4 depicts a coating apparatus for forming a coating on a lead in accordance to an embodiment of the present invention.

As discussed above, each of the layers of the coating 30 can be applied via a solventless coating process onto the outer surface 34 of the lead body 12. According to one embodiment, an automated syringe coating apparatus 100, as shown in FIG. 4, applies the solventless compositions for forming the polymer matrix layer 44, the primer layer 46, the topcoat layer 48 and/or the fluoro-opaque layer 52 to at least a portion of the lead body 12. As shown in FIG. 4, a motorized syringe 102 mounted on a syringe pump 104 is connected to a hypodermic needle based nozzle assembly 106 and is used to apply one or more layers to at least a portion of the lead body 12. In one embodiment, the pump 104 is a positive displacement pump that can accurately meter fluid, the advancement of which is controlled by a motor 105, such as a step motor. The fluid can be dispensed at a predetermined rate and in predetermined amounts. In one embodiment, the amount of fluid dispensed onto the lead body 12 is directly proportional to the thickness of the layer being formed.

According to various embodiments, the lead body 12 is rotated along its longitudinal axis using a rotation apparatus 108 while the coating composition is being dispensed such that all sides of the lead body 12 are coated. In some embodiments, a microscope 110 is attached to the apparatus 100 to assist in visualizing the coating procedure. The lead body 12 can be mounted on the apparatus 100 and positioned under the microscope 110.

Using a syringe coating apparatus 100, as described above, facilitates greater control of coating placement, decreased waste of the coating composition and more uniform coating thickness.

After each individual layer (polymer matrix layer 44, primer layer 46, topcoat layer 48 and/or fluoro-opaque layer 52) is applied to the lead body 12, the layer is cured or allowed to dry prior to application of the next layer. The solventless compositions for forming each of the individual layers can be cured using heat, UV radiation, gamma radiation or other suitable polymer curing techniques known to those of skill in the art.

The coating process, described above, can be repeated as many times as desired to provide for multiple layers. In some embodiments, the total thickness of the coating 30 comprising one or more layers (polymer matrix layer 44, primer layer 46, topcoat layer 48, and/or fluoro-opaque layer 52) ranges from about less than 1 micron to about 200 microns. In another embodiment, the total thickness of the coating 30 ranges from about 1 micron to about 150 microns. In still other embodiments, the total thickness of the coating ranges from about 1 micron to about 100 microns. The thickness of any given individual layer also can range from about 1 micron to about 200 microns and, more particularly, from about 1 micron to about 150 microns. In still other embodiments, the thickness of a given individual layer ranges from about 1 micron to about 100 microns.

Additionally, the thickness of each individual layer (polymer matrix layer 44, primer layer 46, topcoat layer 48 and/or fluoro-opaque layer 52) need not be the same and can vary from layer to layer. For example, the topcoat layer 48 disposed over the fluoro-opaque layer may be a relatively thin layer when compared to the thickness of the fluoro-opaque layer 52. Additionally, in another example, the polymer matrix layer 44 may make up at least 50% or more of the total thickness of the coating 30 with any additional layers (fluoro-opaque 52, primer 46 and/or topcoat layer 48) combining to make up the difference. In another embodiment, the polymer matrix layer 44 and the fluoro-opaque layer 52 together in combination make up at least 50% or more of the total thickness of the coating 30. In other examples, the polymer matrix layer 44 may make up at least 75% or more of the total thickness of the coating 30. The thickness of the individual layers, in particular the fluoro-opaque layer 52 and the polymer matrix layer 44, may be dependent on the amount of additional material admixed therein.

According to various embodiments of the present invention, a therapeutic agent eluting lead 10 can be delivered to a desired site within the patient's body using conventional implantation techniques under visualization. Once implanted, the therapeutic agent elutes from the coating 30 provided on the outer surface 34 of the lead body 12 to treat adjacent tissue. In this manner, the inflammatory process and/or other unwanted biological processes associated with implantation and the presence of the foreign object are suppressed (e.g., reduced inflammation and/or toxicity of inflammatory response).

Additionally, the growth of non-excitable, connective tissue around the electrode (e.g., the capsule) is reduced (e.g., a reduction in fibrotic capsule thickness may be observed), and thus, the postoperative rise in the stimulation threshold lessens, a stable reduced threshold, both acute and chronic, is thereby provided. Additionally, the device and methods may prevent myocyte cell function impairment and/or necrosis around, near or on an electrode 28, which may further stabilize a reduced threshold.

EXAMPLES

Example 1

Solventless Method

Figure 5:
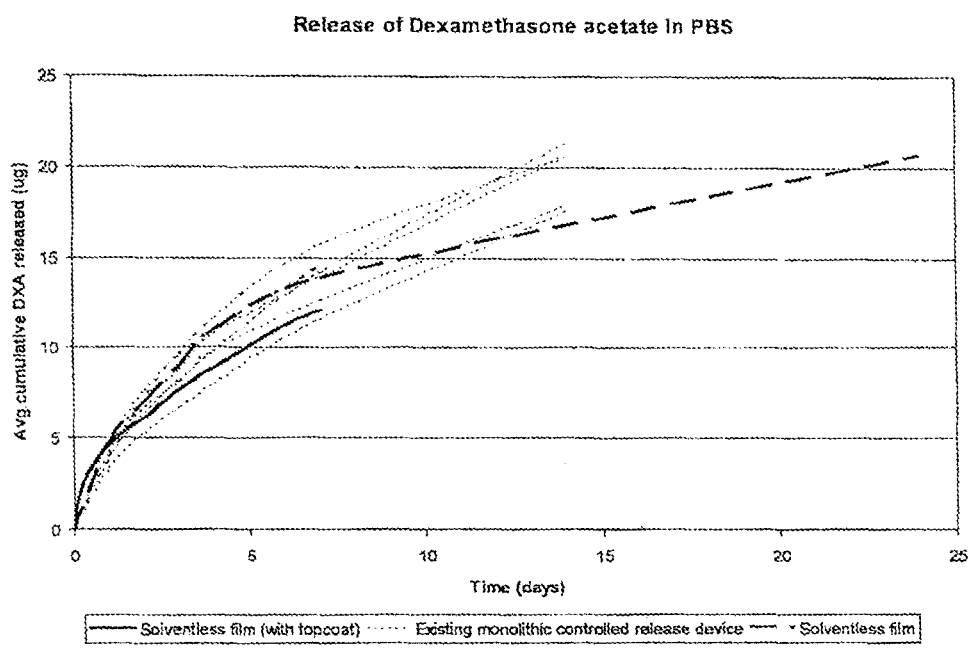
FIG. 5 is a chart comparing the release rate profiles of coated substrates prepared according to various embodiments of the present invention to commercial monolithic release devices.

Uncured NuSil MED-6210 polymer obtained from NuSil Technology LLC, Carpenteria, Calif. was mixed with 20% (wt/wt) dexamethasone acetate (DXA) in a centrifugal mixer to form the solventless coating mixture. Approximately 1-5 µL of the solventless coating mixture was applied to PEEK-coated stainless steel pins using a syringe via a positive displacement pump while the pin was rotated and translated in a longitudinal direction. The solventless coating mixture was cured in situ at 60-75° C. at ambient pressure and atmosphere for 1-3 hours. Some samples were coated with a second topcoat layer of polymer, containing no DXA. The release of DXA from the coated samples was evaluated in phosphate-buffered saline (PBS) over 7-24 days. The average cumulative release for DXA from the 20% (wt/wt) content samples (with and without topcoat) was plotted as a function of time and compared to the release of DXA in PBS for existing commercialized monolithic controlled release devices (FIG. 5). The coated samples exhibited release profiles similar to those exhibited by the existing commercial monolithic release devices known to have in vivo efficacy.

Example 2

Comparison Study

The release of DXA from the samples prepared according to the solventless method described above in Example 1 were then compared to the release of DXA from samples prepared using a conventional, solvent-based method. The solvent-based samples were prepared by first mixing the desired amount of DXA, NuSil MED 6210, and an appropriate solvent in a centrifugal mixer to form the coating mixture. Two coating mixtures were formed. The first coating mixture contained 2% DXA, 10% medical adhesive and the remainder being solvent to produce a coating containing approximately 20% DXA after solvent evaporation. The second coating mixture contained 2% DXA, 20% medical adhesive and the remainder being solvent to produce a coating containing approximately 10% DXA after solvent evaporation. Approximately 1-5 μL of each of the coating mixtures was applied to PEEK-coated stainless steel pins using a syringe via a positive displacement pump while the pin was rotated and translated in a longitudinal direction. The coating mixtures were then cured in-situ at 60-150° C. at ambient pressure and atmosphere for 5 to 60 min or until all the solvent had evaporated off.

Figure 6:
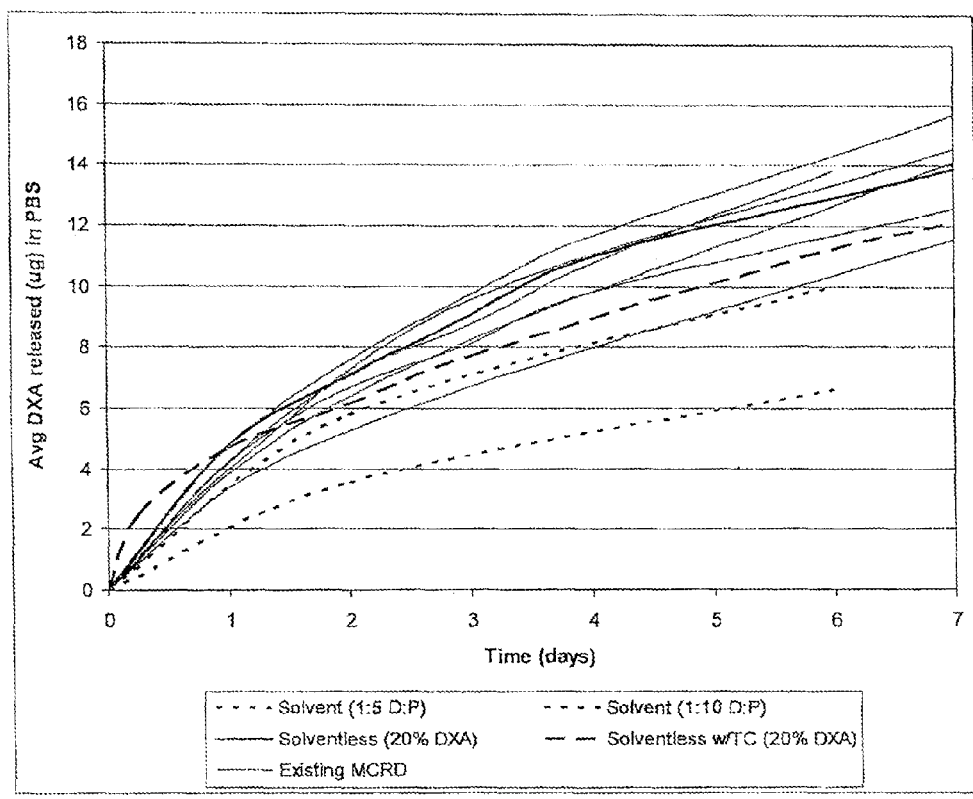
FIG. 6 is a chart comparing the release rate profiles of coated substrates prepared according to various embodiments of the present invention to commercial monolithic release devices and to samples prepared using a solvent-based method.

The release of DXA from the coated pins was evaluated in phosphate-buffered saline (PBS) over 7-24 days. The average cumulative release for DXA from the 2% DXA, 10% matrix and 2% DXA, 20% matrix samples was plotted as a function of time and compared to the release of DXA in PBS for existing commercialized monolithic controlled release devices for perspective as well as those samples prepared using a solventless method (FIG. 6). As demonstrated by the data shown in FIG. 6, those samples prepared using a solventless method exhibited release profiles similar to those exhibited by the existing commercial monolithic release devices known to have in vivo efficacy and those samples prepared using a solvent-based method. Additionally, as expected, the presence of a topcoat layer over the coating mixture suppressed the release of DXA from the coating matrix.

Example 3

Formation of a Fluoro-Opaque Layer

An appropriate amount of monocrystalline tungsten powder was combined with an appropriate amount of NuSil MED 6215 to form a suspension including about 25 wt. % of tungsten. The tungsten powder was mixed with the MED 6215 to provide a uniform suspension using a centrifugal or acoustic mixer. The mixture was then loaded into a 250 uL glass Harvard Apparatus syringe with an EFD tapered tip of varying gauge. The syringe was then loaded into a Harvard Apparatus Nanomite syringe pump. The substrate to be coated (e.g. a molded PEEK shell secured to a stainless steel pin) was then fitted onto an automated coating apparatus, as described in reference to FIG. 4. The suspension was dispensed (0.25-1.0 uL) onto the substrate while the substrate article was rotated and translated automatically to ensure uniform coating. The substrate including the suspension was cured at 60-75° C. for ~60 min to form the fluoro-opaque layer. The process described above was repeated to provide suspensions/layers including about 10 wt. % and 50 wt. % tungsten powder.

Example 4

X-Ray Study

Figure 7:
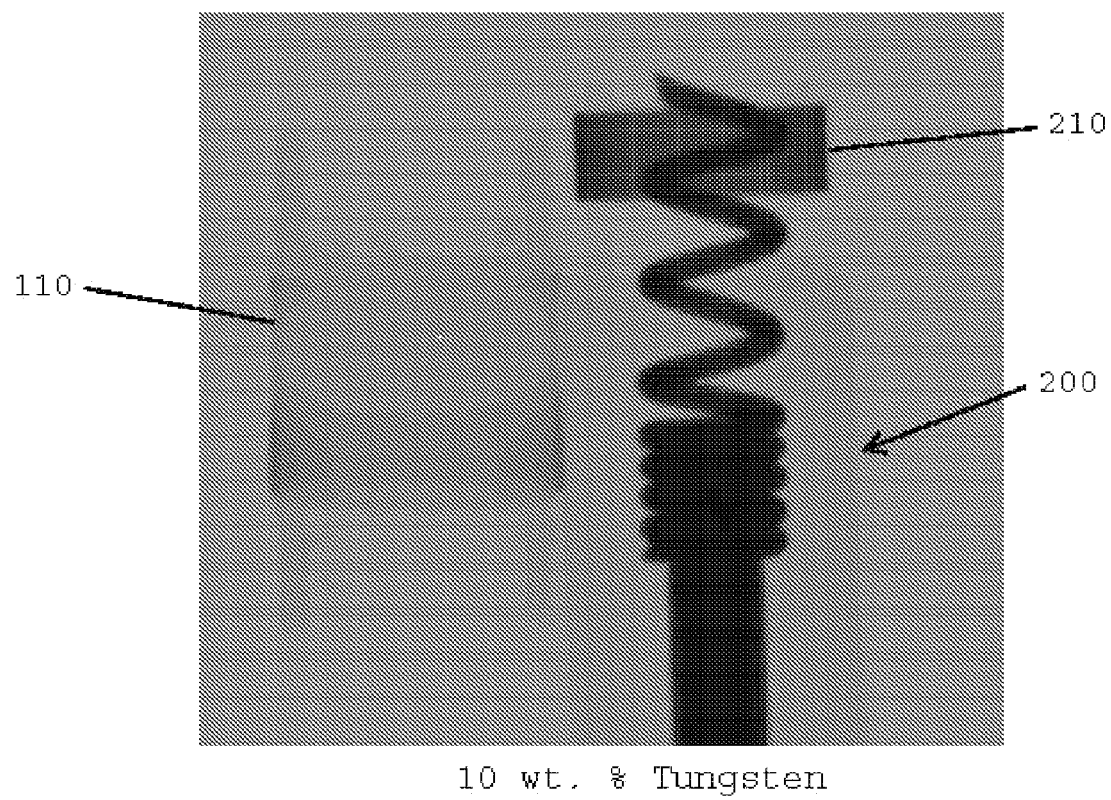
FIGS. 7-9 are photographs taken under X-ray of fluoro-opaque layer samples having different percentages by weight of a fluoro-opaque material.
Figure 8:
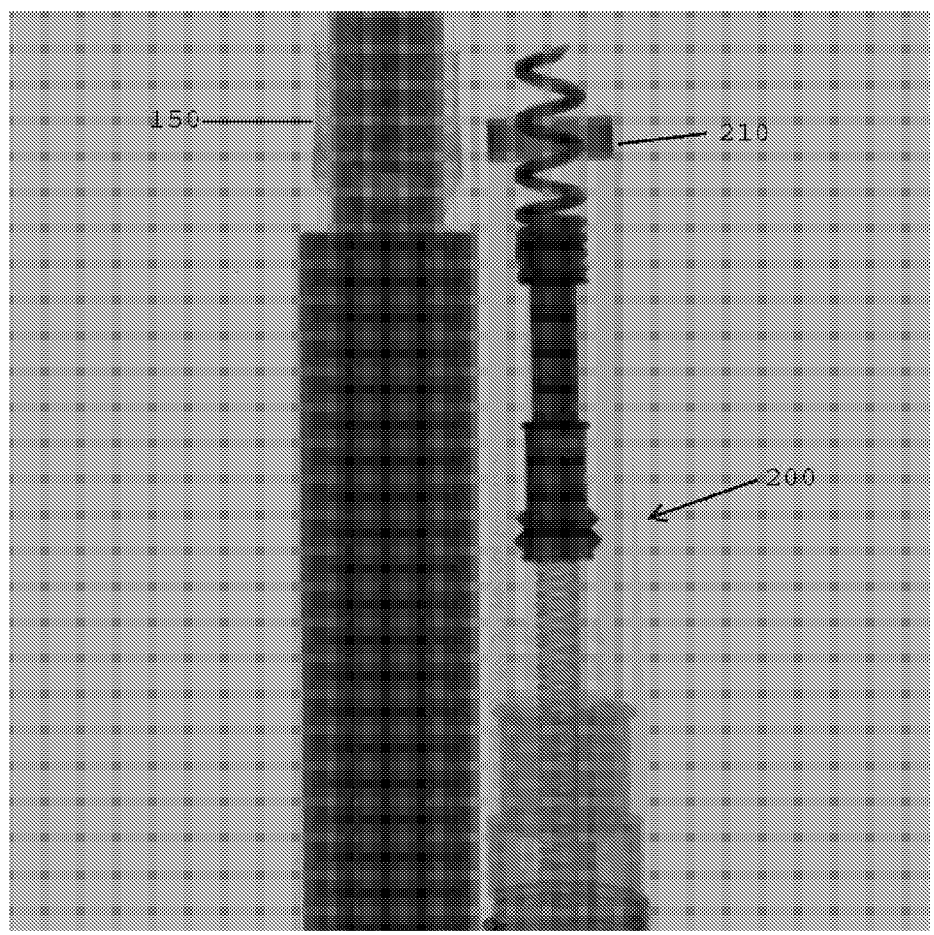
Figure 9:
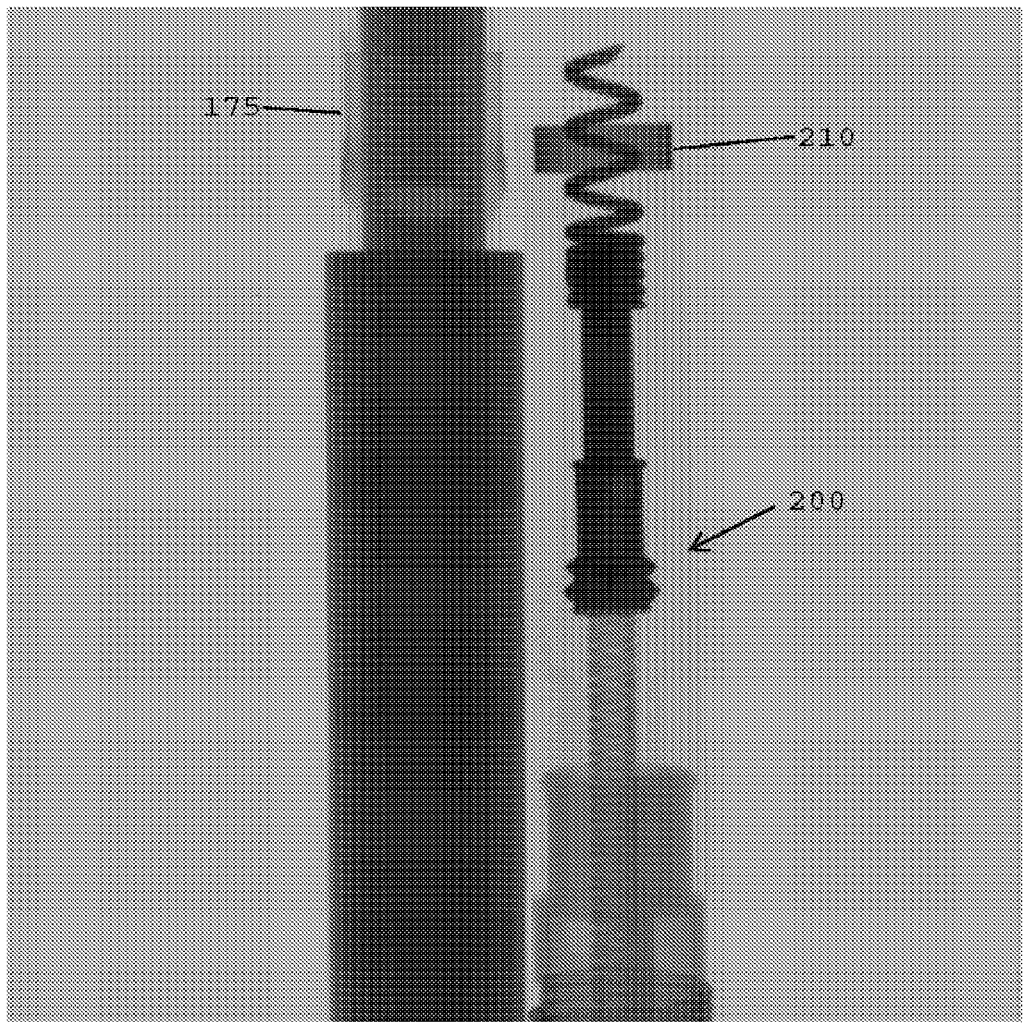

X-ray was used to confirm that the fluoro-opaque layers formed according to the process described above in Example 3 were indeed fluoro-opaque. Each of the 10 wt. %, 50 wt. % and 75 wt. % were visualized under X-ray and their fluoro-opacity compared to each other as well as a standard fluoro-opaque marker found on a commercially available pacing lead, which is a thin ribbon on platinum. FIGS. 7-9 are photos of each of the 10 wt. %, 50 wt. % and 75 wt. % fluoro-opaque layer samples 110, 150 and 175, respectively, with a lead 200 including a standard fluoro-opaque marker 210 for reference. While not as fluoro-opaque as the standard fluoro-opaque marker, each of the fluoro-opaque layers could be seen under X-ray. Additionally, as the weight percentage of tungsten increased, the fluoro-opacity increased, with the 75 wt. % tungsten fluoro-opaque layer being the most radio-opaque. It is anticipated that increasing the number of fluoro-opaque layers, will also increase the fluoro-opacity.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the embodiments, together with all equivalents thereof.

We claim:

1. A solventless method for forming a therapeutic agent eluting coating on a medical electrical lead including a lead body comprising:
   dispensing a predetermined amount of a solventless suspension onto an outer surface of the lead body in close proximity to at least one electrode located on the lead body using an automated syringe while rotating the lead body around its longitudinal axis, the suspension comprising up to about 20 wt % particles of at least one therapeutic agent dispersed within an uncured silicone medical adhesive having a viscosity ranging from about 0.001 Pas to about 20 Pas; and
   moisture curing the suspension to form a polymer matrix layer that is free of residual solvent.

2. The method according to claim 1, wherein the therapeutic agent comprises an anti-inflammatory agent.

3. The method according to claim 1, wherein the therapeutic agent comprises an anti-proliferative agent.

4. The method according to claim 1, wherein the therapeutic agent comprises a combination of an anti-inflammatory agent and an anti-proliferative agent.

5. The method according to claim 1, wherein the therapeutic agent comprises dexamethasone or a derivative or salt thereof.

6. The method according to claim 1, wherein the suspension further comprises particles of a fluoro-opaque material.

7. The method according to claim 6, wherein the fluoro-opaque material comprises tungsten particles.

8. The method according to claim 6, wherein the fluoro-opaque material comprises platinum particles.

9. The method according to claim 1, further comprising the steps of:
   dispensing a predetermined amount of an uncured admixture substantially free of solvent comprising an uncured silicone adhesive having a viscosity ranging from about 0.001 Pas to about 20 Pas and particles of a fluoro-opaque material onto the outer surface of the lead body at a location in close proximity to the at least one electrode using a motorized syringe while rotating the lead body around its longitudinal axis; and curing the admixture to form a fluoro-opaque layer.

10. The method according to claim 9, wherein the fluoro-opaque material comprises tungsten or platinum particles.

11. The method according to claim 9, wherein an amount of fluoro-opaque particles in the admixture ranges from about 10 wt % to about 80 wt %.

12. The method according to claim 9, wherein an amount of fluoro-opaque particles in the admixture is at least 50 wt %.

13. The method according to claim 9, wherein an amount of fluoro-opaque particles in the admixture ranges from about 50 wt % to about 75 wt %.

14. The method according to claim 9, wherein the fluoro-opaque layer is formed over the polymer matrix layer.

15. The method according to claim 9, wherein the polymer matrix layer is formed over the fluoro-opaque layer.

16. The method according to claim 9, wherein the fluoro-opaque layer is formed over and in contact with the outer surface of the lead body.

17. The method according to claim 9, further comprising the steps of:

dispensing a predetermined amount of an uncured topcoat material in the absence of solvent onto the fluoro-opaque layer using a motorized syringe while simultaneously rotating the lead body; and curing the topcoat material to form a topcoat layer disposed over and in contact with the fluoro-opaque layer.

18. The method according to claim 1, further comprising the steps of:

dispensing a predetermined amount of a primer material substantially free of solvent onto the outer surface of the lead body at a location in close proximity to the at least one electrode using a motorized syringe while rotating the lead body around its longitudinal axis;

curing the primer material to form a primer layer; and thereafter, forming the polymer matrix layer over the primer layer.

19. The method according to claim 1, further comprising dispensing a predetermined amount of a primer material substantially free of solvent onto the outer surface of the lead body at a location in close proximity to the at least one electrode using a motorized syringe while rotating the lead body around its longitudinal axis, curing the primer material to form a primer layer, and thereafter forming a fluoro-opaque layer over and in contact with the primer layer.

20. The method according to claim 1, further comprising dispensing a predetermined amount of an uncured topcoat material in the absence of solvent onto the polymer matrix layer using a motorized syringe while simultaneously rotating the lead body.

21. The method according to claim 1, wherein a percentage of therapeutic agent in the suspension ranges from about 2 to about 20% (wt/wt).

22. A solventless method of forming a multi-layered coating on a medical electrical lead including a lead body comprising:

dispensing a predetermined amount of a solventless admixture comprising an uncured silicone adhesive having a viscosity ranging from about 0.001 Pas to about 20 Pas and particles of a fluoro-opaque material onto the outer surface of the lead body at a location in close proximity to the at least one electrode while rotating the lead body around its longitudinal axis;

curing the admixture to form a fluoro-opaque layer, wherein the fluoro-opaque layer comprises about 10 wt % to about 80 wt % of the fluoro-opaque material;

dispensing a predetermined amount of a solventless suspension comprising up to about 20% (wt/wt) of therapeutic agent particles distributed within the uncured silicone medical adhesive having a viscosity ranging from about 0.001 Pas to about 20 Pas over the fluoro-opaque layer using an automated syringe while rotating the lead body around its longitudinal axis; and curing the suspension to form a polymer matrix layer that is free of residual solvent.

23. The method according to claim 22, further comprising dispensing a predetermined amount of an uncured topcoat material in the absence of solvent onto the fluoro-opaque layer using a motorized syringe while simultaneously rotating the lead body; and curing the topcoat material to form a topcoat layer disposed over and in contact with the fluoro-opaque layer.

24. The method of claim 22, further comprising dispensing a predetermined amount of a primer material substantially free of solvent onto the outer surface of the lead body at a location in close proximity to the at least one electrode using a motorized syringe while rotating the lead body around its longitudinal axis, curing the primer material to form a primer layer, and thereafter forming the fluoro-opaque layer over and in contact with the primer layer.

* * * * *